(12) United States Patent
Jansson et al.

(10) Patent No.: US 7,589,208 B2
(45) Date of Patent: Sep. 15, 2009

(54) COMPOSITIONS CONTAINING QUINOLINE COMPOUNDS

(75) Inventors: Karl Jansson, Dalby (SE); Tomas Fristedt, Helsingborg (SE); Hans Wännman, Ängelholm (SE); Anders Björk, Bjärred (SE)

(73) Assignee: Active Biotech AB, Lund (SE)

( * ) Notice: Subject to any disclaimer, the term of this patent is extended or adjusted under 35 U.S.C. 154(b) by 604 days.

(21) Appl. No.: 11/050,441

(22) Filed: Feb. 4, 2005

(65) Prior Publication Data

US 2005/0192315 A1 Sep. 1, 2005

(30) Foreign Application Priority Data

Feb. 6, 2004 (SE) .................... 0400235

(51) Int. Cl.
*C07D 215/38* (2006.01)
(52) U.S. Cl. .................. 546/155; 546/159; 546/153
(58) Field of Classification Search ................ 546/155, 546/153, 159; 514/312
See application file for complete search history.

(56) References Cited

U.S. PATENT DOCUMENTS

| | | | |
|---|---|---|---|
| 4,107,310 A | 8/1978 | Allais et al. | |
| 4,547,511 A | 10/1985 | Eriksoo | |
| 5,716,638 A | 2/1998 | Touitou | |
| 6,077,851 A | 6/2000 | Bjoerk et al. | |
| 6,121,287 A | 9/2000 | Bjoerk et al. | |
| 6,133,285 A | 10/2000 | Bjoerk et al. | |
| 6,395,750 B1 * | 5/2002 | Hedlund et al. | 514/312 |

FOREIGN PATENT DOCUMENTS

| | | | |
|---|---|---|---|
| EP | 0497740 A1 | 8/1992 | |
| WO | WO 9015052 A1 | 12/1990 | |
| WO | 97/23200 A1 | 7/1997 | |
| WO | WO 0003991 A1 | 1/2000 | |
| WO | WO 0003992 A1 | 1/2000 | |
| WO | WO 0130758 A1 | 5/2001 | |
| WO | WO 03106424 A1 | 12/2003 | |

OTHER PUBLICATIONS

Merck Index, 12$^{th}$ Ed. No. 8418.

* cited by examiner

*Primary Examiner*—D. Margaret Seaman
(74) *Attorney, Agent, or Firm*—Browdy & Neimark, P.L.L.C.

(57) ABSTRACT

A stable solid pharmaceutical composition consisting essentially of an effective amount of a salt of formula (II)

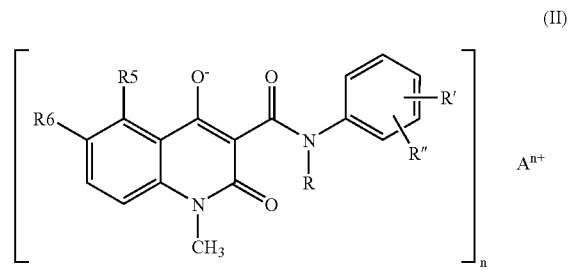

together with an alkaline-reacting component maintaining the pH preferably above 8, or a salt with a divalent metal cation; and
at least one pharmaceutical excipient;
said salt of formula (II) being essentially stable during storage at room temperature for a period of at least 3 years. A process for stabilizing the salt of formula (II).

A crystalline salt of formula (II) and a process for preparing said salt.

32 Claims, No Drawings

COMPOSITIONS CONTAINING QUINOLINE COMPOUNDS

FIELD OF THE THE INVENTION

The present invention relates to stable compositions containing a salt of a 3-quinoline-carboxamide derivative, to methods for the manufacture of such a salt and to methods for the manufacture of a solid pharmaceutical formulation with enhanced stability during long-term storage at room temperature.

BACKGROUND OF THE INVENTION

3-Quinolinecarboxamide derivatives are described in U.S. Pat. Nos. 4,547,511, 6,077,851, 6,133,285 and 6,121,287. The term "3-quinolinecarboxamide derivative" as used in this specification designates the undissociated acid form, hereinafter called the neutral form, of the compound of formula (I), i.e., the form as given in the formula (I).

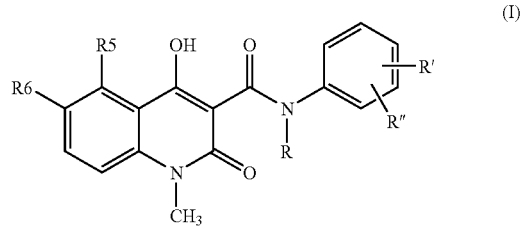

It was unexpectedly found that some 3-quinolinecarboxamide derivatives in the neutral form disclosed in the above US patents are susceptible to chemical degradation in solid state, and, in particular, when in pharmaceutical formulations. Some salts of the 3-quinoline-carboxamide derivatives of formula (I) are known from said US patents. However, none of the above-mentioned patent specifications discloses an enabling method of providing 3-quinoline-carboxamide derivatives of formula (I) susceptible to degradation in a sufficiently stable pharmaceutical form or even suggests any particular advantage of using the salt form of a 3-quinolinecarboxamide derivative in pharmaceutical formulations.

SUMMARY OF THE INVENTION

In accordance with the present invention, there is provided a stable solid pharmaceutical formulation that contains a salt of a 3-quinolinecarboxamide derivative of formula (I) with a monovalent or multivalent cation and a process for preparing said formulation. The process comprises forming a capsule or a tablet containing a salt of a 3-quinolinecarboxamide derivative and a uniformly distributed alkaline-reacting component capable of neutralising any protons dissociating from the excipients, thereby keeping the 3-quinolinecarboxamide in the salt form of formula (II).

Alternatively, the process comprises forming a capsule or a tablet containing a salt of a 3-quinolinecarboxamide derivative sparingly soluble in water and a salt with a divalent metal cation capable of lowering the dissociation of a salt of formula (II) into ions.

The alkaline-reacting component of this invention is typically sodium carbonate, and the salt with a divalent metal cation is typically calcium acetate. The solid formulation of the invention includes pharmaceutical excipients, such as solid powdered carriers, binders, disintegrants and lubricating agents.

The invention additionally provides a process for the manufacture of a crystalline salt of a 3-quinolinecarboxamide derivative of formula (I) with a counter ion that is a multivalent metal cation.

The present invention solves the problem posed by those 3-quinolinecarboxamide derivatives that are susceptible to chemical degradation in a solid pharmaceutical formulation.

DESCRIPTION OF THE INVENTION

Some 3-quinolinecarboxamide derivatives in the neutral form disclosed in the above U.S. patents are susceptible to chemical degradation in solid state, and, in particular, when in pharmaceutical formulations. A primary object of the present invention is to overcome this stability problem. The solution offered by the present invention to said stability problem is based on the surprising and unexpected finding that the salt form of a compound of formula (I) possesses an enhanced chemical stability compared to the neutral form of said compound.

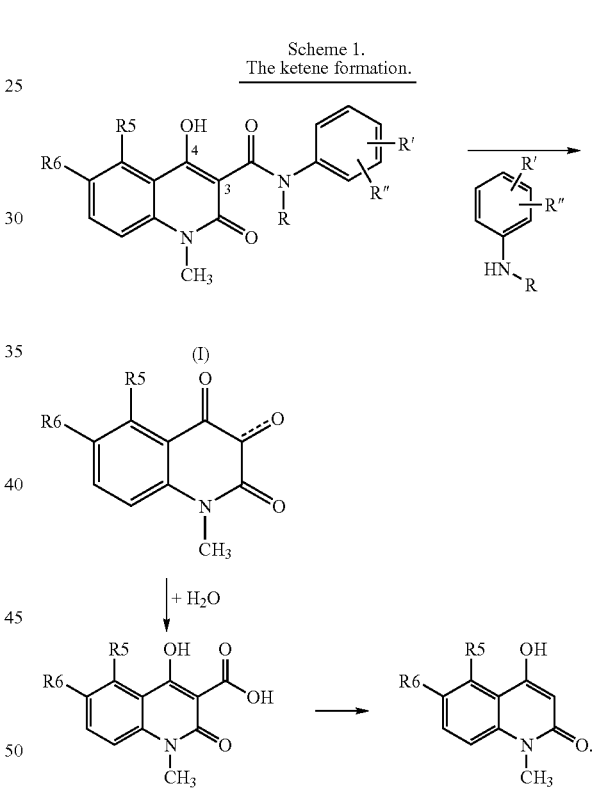

The degradation of the compounds of formula (I) was carefully investigated. The present inventors have demonstrated that the aniline moiety of the compound of formula (I) unexpectedly is eliminated and a highly reactive ketene is formed. This ketene reacts rapidly with, for example, ROH compounds.

Upon storage without any special precautions being taken, some 3-quinolinecarboxamide derivatives of formula (I) are degraded at an unacceptable rate. At storage during accelerated conditions, that is 40° C. and a relative humidity of 75%, the degradation of some 3-quinoline-carboxamide derivatives can exceed 2% in a period of 6 months (Table 1). While the rate of decomposition of 3-quinolinecarboxamide derivatives of formula (I) at normal storage conditions is lower, it nevertheless is desirable to obtain a physical form of a 3-quinoline-carboxamide derivative, which exhibits improved stability.

Surprisingly and unexpectedly it has now been found that the 3-quinolinecarboxamide derivatives of formula (I), when converted to a salt form with a mono- or multivalent metal cation of the structural formula (II),

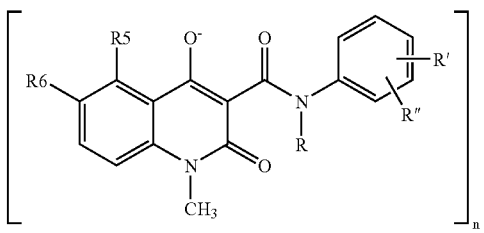

(II)

wherein
n is an integer of 1, 2 or 3;
$A^{n+}$ is a mono- or multivalent metal cation selected from $Li^+$, $Na^+$, $K^+$, $Mg^{2+}$, $Ca^{2+}$, $Mn^{2+}$, $Cu^{2+}$, $Zn^{2+}$, $Al^{3+}$ and $Fe^{3+}$;
R is a straight or branched $C_1$-$C_4$-alkyl or -alkenyl or a cyclic $C_3$-$C_4$-alkyl;
R5 is a straight or branched, saturated or unsaturated $C_1$-$C_4$-alkyl or -alkenyl, a cyclic $C_3$-$C_4$-alkyl, a straight or branched $C_1$-$C_4$-alkylthio, a cyclic $C_3$-$C_4$-alkylthio, a straight or branched $C_1$-$C_4$-alkylsulfinyl, a cyclic $C_3$-$C_4$-alkylsulfinyl, fluoro, chloro, bromo, trifluoromethyl or trifluoromethoxy; and
R6 is hydrogen; or
R5 and R6 taken together are methylenedioxy,
R' is hydrogen, a straight or branched, saturated or unsaturated $C_1$-$C_4$-alkyl or -alkenyl or a cyclic $C_3$-$C_4$-alkyl, a straight or branched $C_1$-$C_4$-alkoxy, a cyclic $C_3$-$C_4$-alkoxy, fluoro, chloro, bromo or trifluoromethyl; and
R" is hydrogen, fluoro or chloro, with the proviso that R" is fluoro or chloro only when R' is fluoro or chloro;
have an enhanced stability compared to the corresponding neutral form of the 3-quinolinecarboxamides of formula (I).

A preferred group of 3-quinolinecarboxamide salts of formula (II) are those wherein $A^{n+}$ is $Li^+$, $Na^+$ and $Ca^{2+}$.

Another preferred group of 3-quinolinecarboxamide salts of formula (II) are those salts sparingly soluble in water including $Ca^{2+}$, $Zn^{2+}$ and $Fe^{3+}$ salts.

A salt of formula (II) of a 3-quinolinecarboxamide is prepared by reacting a 3-quinoline-carboxamide of formula (I) with a mono- or multivalent metal salt. Examples of such salts and reaction conditions are given below. In general, the aqueous solubility of salts of formula (II) is higher for the salts with monovalent cations, e.g., a sodium- or potassium-salt, than for the salts with multivalent cations, e.g., a calcium, zinc, copper(II) or iron(III) salt. As an example the sodium salts are readily soluble in water but they have a limited solubility in less polar solvents, e.g., chloroform. On the contrary, an iron(III) salt is almost insoluble in water but has a high solubility in chloroform and a low solubility in methanol. When using solely aqueous solvent for the precipitation of a multivalent salt, e.g., a calcium salt of formula (II), an amorphous precipitate may form because of the very low solubility in water. However, by increasing the temperature and by adding a water miscible organic solvent, e.g., ethanol, in which the salt has somewhat higher but still a limited solubility, a crystalline compound can be precipitated. Preferably mixtures of water and ethanol, containing 10- 95% ethanol are used to ensure crystalline compounds. In such mixtures the particle size of the precipitate depends on the reaction temperature, the higher temperature results in larger crystals. The reaction temperature can vary from 0° C. up to the reflux temperature. Alternatively, a crystalline salt can be prepared from an amorphous salt by mixing with a solvent in which the crystalline compound has a limited solubility as demonstrated in EXAMPLES 4 and 7.

The storage stability of a compound of formula (II) is greatly improved. This is evident from a comparison of N-ethyl-N-phenyl- 5-chloro- 1,2-dihydro- 4-hydroxy- 1-methyl- 2-oxo- 3-quinolinecarboxamide (hereinafter called compound A) with the sodium salt of N-ethyl-N-phenyl- 5-chloro- 1,2-dihydro- 4-hydroxy- 1-methyl- 2-oxo- 3-quinolinecarboxamide (hereinafter called compound A sodium). While at 40° C. and a relative humidity of 75% less than 0.01% of compound A sodium in solid state is converted to degradation products in a period of 24 months, 0.31% of compound A is degraded during a 6-month period. Another example of a 3-quinolinecarboxamide derivative susceptible to degradation is N-ethyl-N-phenyl- 5-ethyl- 1,2-dihydro- 4-hydroxy- 1-methyl- 2-oxo- 3-quinolinecarboxamide (hereinafter called compound B), see Table 1.

TABLE 1

Stability of 3-quinolinecarboxamide derivatives.
Storage conditions: +40° C./75% RH.

| Compound | Degradation[1] | "Shelf-life"[2] |
| --- | --- | --- |
| A | 0.31% | >6 months |
| A sodium | <0.01%[3] | >6 months |
| B | 2.0% | <1 months |

[1]Degradation quantified as the percentage increase of related substances after 6 months of storage.
[2]"Shelf life" denotes how long the compound can be stored at the given conditions without degradation exceeding 0.5%:
[3]The same result is obtained after 24 months of storage.

Generally, any tendency of instability is exacerbated when a compound of formula (II) is formulated with various excipients. This is verified by the results from a compatibility study comparing compound A with compound A sodium shown in Table 2. It is clear that the salt form is preferred as drug substance in any binary mixtures of said compound.

TABLE 2

Compatibility studies comparing compound A with compound A sodium.
The samples are binary mixtures (1:1) of excipient and test substance.
Storage conditions: +40° C./75% RH.

| Excipient | Degradation[1] (Compound A) | Degradation[1] (Compound A sodium) |
| --- | --- | --- |
| Microcrystalline Cellulose (Avicel PH-101) | 1.1% | 0.31% |
| Maize Starch | 0.41% | 0.05% |
| Mannitol (Pearlitol 200SD) | 0.45% | 0.05% |
| Colloidal silica (Aerosil 200) | 20% | 1.5% |

[1]Degradation quantified as the percentage increase of related substances after 6 months of storage.

Said sodium salt when formulated into conventional solid pharmaceutical formulation, however, is still degraded at an unacceptable rate with a level of degradation products exceeding 5% in 6 months when stored at +40° C. and a relative humidity of 75% (Table 3). Such a level is considered problematic. An acceptable limit of degradation, under these conditions, is judged to be less than 0.5% degradation after 6 months storage. This limit is considered indicative of a 3-year shelf-life at room temperature. On the other hand, a conventional solid pharmaceutical formulation with an alkaline-reacting component also shows an unacceptable rate of degradation. The crucial step is to obtain a uniform distribution of the salt of formula (II), the alkaline-reacting component and all the pharmaceutical excipients on a molecular level.

TABLE 3

Stability data from different formulations of compound A sodium.

| Formulation | Storage conditions | Degradation[1] | "Shelf life"[2] |
|---|---|---|---|
| Aqueous solution[3] | +2° C. to +8° C. | <0.01% | >6 months |
| Conventional tablet formulation[4] (reference) | +40° C./75% RH | 6.8% | <0.5 month |
| Conventional tablet formulation with an alkaline-reacting component[5] (reference) | +40° C./75% RH | 0.64%[7] | 1 month |
| EXAMPLE 10[6] (invention) | +40° C./75% RH | 0.16% | >6 months |

[1]Degradation quantified as the percentage increase of related substances after 6 months of storage.
[2]"Shelf life" denotes how long the formulation can be stored at the given conditions without degradation exceeding 0.5%.
[3]Composition: Compound A sodium 1 mg, sodium hydroxide 0.112 mg, water for injection ad 1 ml, pH adjusted to 7.5.
[4]Composition: Compound A sodium 0.3 mg (0.19%), microcrystalline cellulose 49.8%, lactose monohydrate 48.5%, sodium croscarmellose 0.5%, sodium stearyl fumarate 1%.
[5]Composition: Compound A sodium 0.3 mg (0.19%), pregelatinised starch 66%, mannitol 29.8%, sodium carbonate 3.0%, sodium stearyl fumarate 1.0%.
[6]Composition: According to EXAMPLE 10.
[7]Formation of related substances after 2 months of storage.

The present invention provides compositions of a salt form of a 3-quinolinecarboxamide derivative, such compositions exhibiting improved storage stability that allows the development of new pharmaceutical formulations of a 3-quinolinecarboxamide with enhanced stability during long-term, i.e., at least 3 years, storage at room temperature.

Here, the expression a "3-quinolinecarboxamide derivative susceptible to degradation" should be taken to mean a substance with a reactivity index >1.0 (see EXAMPLES, Investigation of the degradation rate below). Mechanistic studies of the ketene degradation have shown that the degradation involves an intramolecular transfer of the enol proton in the 4-position of the quinoline ring to the nitrogen atom of the 3-carboxamide moiety (Scheme 1). It is envisaged that a stable dosage form of a compound of formula (I) would be obtained if said compound is converted to the salt form of formula (II). However, notwithstanding the enhanced chemical stability of said salt in the solid state, there still remains an unacceptable degree of instability in conventional solid dosage forms of the salts of formula (II). The reason for the instability of salts of formula (II) in conventional solid dosage forms is now believed to be linked to the exchange of the counter ion for a proton combined with the conformation of the salt in the solid state.

X-ray studies of the sodium salt of compound A demonstrated that the conformation of the solid salt is such that the exocyclic carbonyl group is bent away from the enolate oxygen atom in the 4-position. This leads to an open path between the nitrogen atom of the 3-carboxamide moiety and the enolate sodium atom in the 4-position. Without wishing to be bound to any theory of action, it is thought that this conformational property of the salts of formula (II) results in the unacceptable rate of degradation in conventional solid dosage forms once the counter ion of the salt is exchanged with a proton obtainable from the excipients.

From what is said above about the stability properties of 3-quinolinecarboxamide derivatives, it is clear that a stable dosage form of a compound of formula (I) is obtained when said compound is present and remains in the salt form of formula (II). For clinical use a salt of formula (II) of the present invention, i.e., the active ingredient, suitably is formulated into pharmaceutical solid formulations for oral mode of administration. The rigorous prevention of any conversion of said salt to the neutral form would lead to improved stability of said salts during manufacture, and during storage of the pharmaceutical formulation. Examples of such formulations are tablets and capsules. Usually the amount of active ingredient is about 0.01 to 10% by weight of the formulation, preferably about 0.1 to 2% by weight of the formulation.

Pharmaceutical compositions of the present invention contain a salt of formula (II) in combination with at least one component inhibiting degradation of tie active ingredient, and pharmaceutical excipients. These compositions are one object of this invention.

In one embodiment of the present invention, the composition comprises an alkaline-reacting component, which neutralises the protons. The amount of the alkaline-reacting component is dependent upon the property of said alkaline-reacting component and is about 0.1 to 99% by weight of the formulation, preferably about 1 to 20%. The pH of a specific composition is determined by adding to 2 g of the composition 4 g of de-ionised water, and then measuring the pH of the resulting slurry. The pH should preferably be above 8. Suitable alkaline-reacting components are selected from sodium, potassium, calcium and aluminum salts of acetic acid, carbonic acid, citric acid, phosphoric acid, sulphuric acid, or other suitable weak inorganic or organic acids.

In another embodiment, the composition comprises a salt with a divalent metal cation, preferably calcium acetate, and a calcium salt of formula (II). Any other salt with a divalent metal cation suitable in view of the intended application of the composition may be used, e.g., zinc and manganese salts. The amount of said salt is about 1 to 99% by weight of the formulation depending on the salt chosen. It is thought that addition of salt containing a divalent metal cation to the pharmaceutical composition would lower the dissociation of the salt of formula (II) into ions. A salt of formula (II) having a divalent metal counter ion has limited solubility. Thus the protonation of the anion of the salt of formula (II) is suppressed, which results in an increased stability.

Compositions and pharmaceutical formulations containing the compounds of formula (II) described above are manufactured as described herein below.

In the preparation of pharmaceutical formulations in the form of dosage units for oral administration, the compound (II) is mixed with a salt with a divalent metal cation or an alkaline-reacting component and with conventional pharmaceutical excipients. Suitable excipients can be chosen among, but are not restricted to, solid powdered carriers, e.g., mannitol, microcrystalline cellulose, calcium hydrogen phosphate, calcium sulphate, and starch; binders, e.g., polyvinylpyrrolidone, starch and hydroxypropyl methylcellulose; disintegrants, e.g., sodium croscarmellose, sodium starch glycollate and polyvinylpyrrolidone as well as lubricating agents, e.g., magnesium stearate, sodium stearyl fumarate, talc and hydrogenated vegetable oil such as Sterotex NF. The mixture is then processed into tablets or granules for capsules.

According to one aspect, the present invention provides a method of preparing a tablet comprising as an active ingredient a 3-quinolinecarboxamide derivative of improved chemical stability wherein a tablet core containing a salt of formula (II) and an alkaline-reacting component, or a salt with a divalent metal cation, as well as suitable pharmaceutical excipients is manufactured. The crucial step is to achieve a tablet core with a uniform distribution, on the molecular level, of the alkaline-reacting component in order to neutralise all protons diffusing from the pharmaceutical excipients, or of the salt with a divalent metal cation in order to suppress the dissociation into ions of the salt of formula (II).

Methods of manufacturing a tablet of the invention are as follows:

a) a tablet core containing a calcium salt of formula (II) is manufactured by spraying a calcium acetate solution onto a mixture of the calcium salt of formula (II) and the pharmaceutical excipients, granulating the mixture to proper consistency, drying, and then compressing the granulate; or b) a tablet core containing a salt of formula (II) sparingly soluble in water is manufactured by spraying a solution of an alkaline-reacting component onto a mixture of the pharmaceutical excipients, granulating the mixture to proper consistency, drying, mixing with a crystalline salt of formula (II) sparingly soluble in water, and then compressing the final blend; or c) a tablet core containing a lithium, sodium or potassium salt of formula (II) is manufactured by spraying a solution of the salt of formula (II) and an alkaline-reacting component onto a mixture of the pharmaceutical excipients, granulating the mixture to proper consistency, drying, and then compressing the granulate; and d) a lubricating agent may optionally be added to the granulate prior to compression; and e) a coating layer is optionally added to said core using conventional coating pharmaceutical excipients.

A preferred method of manufacturing a tablet of the invention is:

f) a tablet core containing a sodium salt of formula (II) is manufactured by spraying a solution of a sodium salt of formula (II) and an alkaline-reacting component onto a mixture of the pharmaceutical excipients, granulating the mixture to proper consistency, drying, and then compressing the granulate. A lubricating agent may optionally be added to the granulate prior to compression, and a coating layer is optionally added to said core using conventional coating pharmaceutical excipients.

According to another aspect, the present invention provides a method of preparing a capsule comprising as an active ingredient a 3-quinolinecarboxamide derivative of improved chemical stability.

Methods of manufacturing a capsule of the invention are as follows:

g) a mixture containing a calcium salt of formula (II) is manufactured by spraying a calcium acetate solution onto a mixture of the calcium salt of formula (II) and the pharmaceutical excipients, granulating the mixture to proper consistency, and subsequently drying the granulate; or h) a mixture containing a salt of formula (II) sparingly soluble in water is manufactured by spraying a solution of an alkaline-reacting component onto a mixture of the pharmaceutical excipients, granulating the mixture to proper consistency, drying the granulate, and mixing with a crystalline salt of formula (II) sparingly soluble in water; or i) a mixture containing a lithium, sodium or potassium salt of formula (II), more preferably a sodium salt, is manufactured by spraying a solution of the salt of formula (II) and an alkaline-reacting component onto a mixture of the pharmaceutical excipients, granulating the mixture to proper consistency, and subsequently drying the granulate;

j) a lubricating agent is optionally added to the mixture; and k) the final blend is filled into hard gelatine capsules.

An alternative method of preparing a salt of formula (II), which then has to be readily soluble in water is to dissolve the corresponding compound of formula (I) in the neutral form in a solution of an alkaline reacting component such as sodium carbonate, thus producing the salt of formula (II) in-situ, and subsequently follow the methods as described above.

EXAMPLES

The examples below are given with the intention to illustrate the invention without limiting, the scope thereof.

Example 1

Investigation of the Degradation Rate

The degradation rate, hereinafter called the reactivity index, of compound of formula (I) was determined in solution. Roquinimex (Merck Index 12th Ed., No. 8418; Linomide®, LS 2616, N-methyl-N-phenyl- 1,2-dihydro- 4-hydroxy- 1-methyl- 2-oxo- 3-quinolinecarboxamide) was selected as a reference compound with the reactivity index defined to 1.0. A medium of 1-% 0.01M hydrochloric acid in n-propanol was selected. The reaction temperature was in the range of 45 to 60° C. The 3-quinolinecarboxamide derivative of formula (I) was added to the n-propanol solution The reaction transfers the compound to an n-propylester. The reaction was stopped after 0, 2 and 4 hours, and analysis was carried out by means of HPLC with UV detection. The disappearance of the 3-quinolinecarboxamide derivative was used for evaluation of the reactivity index, but as an alternative also the formation of the n-propylester may be used. A reactivity index of 1.0 corresponds to a degradation rate of 13% per hour at 60° C., a reactivity index of 2.0 corresponds to a degradation rate of 26% per hour etc. The reactivity indices of some compounds of formula (I) are shown in Table 1.

TABLE 4

Reactivity index of compounds of formula (I).

Structure in relation to compound (I)

| Compound | R5, R6 | R', R" | R | Reactivity index |
| --- | --- | --- | --- | --- |
| Roquinimex | H | H | methyl | 1.0 (defined) |
| A | 5-chloro | H | ethyl | 3.1 |
| B | 5-ethyl | H | ethyl | 4.6 |
| C | 5-chloro | 2,4-$F_2$ | methyl | 2.6 |
| D | 5-methyl | 4-$CF_3$ | methyl | >10 |
| E | 5,6-methylenedioxy | H | ethyl | 2.9 |
| F | 5-methylthio | H | ethyl | >10 |

Compound A is N-ethyl-N-phenyl-5-chloro-1,2-dihydro-4-hydroxy-1-methyl-2-oxo-3-quinolinecarboxamide;
Compound B is N-ethyl-N-phenyl-5-ethyl-1,2-dihydro-4-hydroxy-1-methyl-2-oxo-3-quinolinecarboxamide;
Compound C is N-methyl-N-(2,4-difluorophenyl)-5-chloro-1,2-dihydro-4-hydroxy-1-methyl-2-oxo-3-quinolinecarboxamide;
Compound D is N-methyl-N-(4-trifluorophenyl)-1,2-dihydro-1,5-dimethyl-4-hydroxy-1-methyl-2-oxo-3-quinolinecarboxamide;
Compound E is N-ethyl-N-phenyl-5,6-methylenedioxy-1,2-dihydro-4-hydroxy-1-methyl-2-oxo-3-quinolinecarboxamide; and
Compound F is N-ethyl-N-phenyl-5-methylthio-1,2-dihydro-4-hydroxy-1-methyl-2-oxo-3-quinolinecarboxamide.

The following detailed Examples 2 to 7 serve to illustrate the process for manufacturing the compounds of formula (II), which are used in the pharmaceutical formulations according to the present invention.

Example 2

N-Ethyl-N-phenyl- 5-chloro- 1,2-dihydro- 4-hydroxy- 1-methyl- 2-oxo- 3-quinolinecarboxamide sodium salt N-Ethyl-N-phenyl- 5-chloro- 1,2-dihydro- 4-hydroxy- 1-methyl- 2-oxo- 3-quinolinecarboxamide ( 28 mmol, 10.0 g) was suspended in 99.5% ethanol ( 150 ml) and 5 M aqueous sodium hydroxide solution ( 28.4 mmol, 5.68 ml) was added. The reaction mixture was stirred for 30 minutes at ambient temperature. The resulting crystalline precipitate was isolated by filtration, rapidly washed twice with cold ethanol ( 2×150 ml), and dried in vacuum over $P_2O_5$ to give the title compound ( 9.5 g, 90% yield). Anal. Calcd for $C_{19}H_{16}ClN_2O_3Na$: C, 60.2; H, 4.26; N, 7.40. Found C, 60.4; H, 4.20; N, 7.32.

The solubility in water at room temperature was 138 mg/ml.

Example 3

N-Ethyl-N-phenyl- 5-chloro- 1,2-dihydro- 4-hydroxy- 1-methyl- 2-oxo- 3-quinolinecarboxamide calcium salt N-Ethyl-N-phenyl- 5chloro- 1,2-dihydro- 4-hydroxy- 1-methyl- 2-oxo- 3-quinolinecarboxamide sodium salt ( 2.63 mmol, 1.0 g) was dissolved in a mixture of ethanol ( 10.5 ml) and water ( 5.3 ml). The solution was heated to 70° C. and a solution of calcium acetate hydrate in water ( 1M solution, 1.05 eq., 1.38 mmol, 1.38 ml) was added. The resulting suspension was stirred for 30 minutes, then cooled, and the crystals were isolated by filtration, washed with water, and dried under vacuum ( 966 mg, 98% yield). Anal. Calcd for $C_{38}H_{32}Cl_2N_4O_6Ca$: C, 60.7; H, 4.29; N, 7.45. Found C, 60.5; H, 4.34; N, 7.41.

The solubility in water at room temperature was about 1.0 mg/ml. The salt is considered as sparingly soluble in water.

Example 4

N-Ethyl-N-phenyl- 5-chloro- 1,2-dihydro- 4-hydroxy- 1-methyl- 2-oxo- 3-quinolinecarboxamide iron (III) salt N-Ethyl-N-phenyl- 5-chloro- 1,2-dihydro- 4-hydroxy- 1-methyl- 2-oxo- 3-quinolinecarboxamide sodium salt ( 5.0 g 13.2 mmol) was dissolved in water ( 80 ml) at 40° C. and chloroform ( 100 ml) was added. A solution of iron(III)sulphate pentahydrate ( 0.95 eq., 2.09 mmol, 1.023 g) dissolved in water ( 30 ml) was added. The two-phase system was stirred vigorously and pH in the aqueous phase was adjusted to 8 with 1 M NaOH. The deep-red organic phase was separated, dried with sodium sulphate, and solvents were removed to give the title compound as a red amorphous glassy mass ( 4.22 g, 85% yield). MS-ESI: m/z 1122 [MH]+. The glassy mass was dissolved in methanol and red crystals of the title compound were formed. The crystals were filtered, washed with methanol, and dried under vacuum to give the title compound ( 3.96 g, 80% yield). Anal. Calcd for $C_{57}H_{48}N_6O_9Cl_3Fe$: C, 61.0; H, 4.31; N, 7.48. Found C, 62.7; H, 4.37; N, 7.27. EDTA-titriometric determination of iron (III) gave a content of 4.90% (theoretical content is 4.97%).

Example 5

N-Ethyl-N-phenyl- 5-ethyl- 2-dihydro- 4-hydroxy- 1-methyl- 2-oxo- 3-quinolinecarboxamide lithium salt N-Ethyl-N-phenyl- 5-ethyl- 1,2-dihydro- 4-hydroxy- 1-methyl- 2-oxo- 3-quinolinecarboxamide ( 4.39 mmol, 1.539 g) was suspended in ethanol ( 7.5 ml) and a solution of lithium hydroxide hydrate ( 1.05 eq. 4.61 mmol, 195 mg) dissolved in water ( 1.5 ml) was added. The mixture was stirred for 4 h and ethyl acetate ( 30 ml) was added. After stirring for 1 h the crystals were filtered, washed with ethyl acetate, and dried under vacuum to furnish the title product ( 1.31 g, 84% yield). Anal. Calcd for $C_{21}H_{21}N_2O_3Li$: C, 70.8; H, 5.94; N, 7.86. Found C, 70.5; H, 5.22; N, 8.01

The solubility in water at room temperature was 18 mg/ml.

Example 6

N-Ethyl-N-phenyl- 5-ethyl- 1,2-dihydro- 4-hydroxy- 1-methyl- 2-oxo- 3-quinolinecarboxamide calcium salt N-Ethyl-N-phenyl- 5-ethyl- 1,2-dihydro- 4-hydroxy- 1-methyl- 2-oxo- 3-quinolinecarboxamide ( 5.0 g, 14.2 mmol) was dissolved in a mixture of 1M NaOH ( 14.26 mmol, 14.26 ml) and ethanol ( 30 ml), and pH was adjusted to 7.5. The solution was heated to 70° C. and calcium acetate hydrate ( 1.05 eq., 7.5 mmol, 1.335 g) in water ( 7 ml) was added dropwise during 5 min. The heating was discontinued and the mixture was stirred at room temperature for 1 h, the crystals were filtered, washed with ethanol/water 1/1 and dried under vacuum to afford the title compound ( 5.16 g, 98% yield). Anal. Calcd for $C_{42}H_{42}N_4O_6Ca$: C, 68.3; H, 5.73; N, 7.58. Found C, 68.4; H, 5.72; N, 7.63. EDTA-titriometric determination of calcium gave a content of 5.42% (theoretical content is 5.42%).

The solubility in water at room temperature was 0.3 mg/ml.

Example 7

N-Ethyl-N-phenyl- 5-ethyl- 1,2-dihydro- 4-hydroxy- 1-methyl- 2-oxo- 3-quinolinecarboxamide zinc salt N-Ethyl-N-phenyl- 5-ethyl- 1,2-dihydro- 4-hydroxy- 1-methyl- 2-oxo- 3-quinolinecarboxamide ( 1.0 g, 2.85 mmol) was dissolved in a mixture of 1M NaOH ( 2.95 mmol, 2.95 ml) and ethanol ( 6.0 ml). Chloroform ( 20 ml) and water ( 40 ml) were added followed by addition of zinc acetate dihydrate ( 3.0 mmol, 660 mg). The two-phase mixture was stirred vigorously for 10 min, the organic phase was separated and dried with sodium sulphate and the solvents were removed. The residue was recrystallised from methanol to give the title compound ( 823 mg, 76% yield). Anal. Calcd for $C_{42}H_{42}N_4O_6Zn$: C, 66.01; H, 5.54; N, 7.33. Found C, 65.4; H, 5.68; N, 7.29. EDTA-titriometric determination of zinc gave a content of 8.45% (theoretical content is 8.56%).

The solubility in water at room temperature was 0.3 mg/ml.

Example 8

Description of Manufacturing

A pharmaceutical formulation according to the present invention, in the form of capsules, having the following composition was prepared:

| | Granulate 0.17% | |
|---|---|---|
| Solid excipients | Mannitol | 96.8% |
| | Sodium carbonate | 3.00% |
| Granulation fluid | Compound A sodium[1] | 0.18% |
| | Sodium carbonate | 0.03% |
| | Water (13.3% of solid excipients) | na[2] |
| | Capsules | |
| Final blend | Compound A sodium Granulate 0.17% | 99.0% |
| | Sodium stearyl fumarate | 1.00% |

[1]The compound given above may be replaced with another compound of the present invention.
[2]The water is removed during drying.

Compound A sodium was dissolved in aqueous sodium carbonate and wet granulated together with mannitol and additional sodium carbonate. All excipients required for capsule filling except the lubricant were present in the granulation step. The resulting granulate was dried in a conventional manner and passed through a screen of suitable size. The dry granules were mixed well with sodium stearyl fumarate and the mixture obtained was filled into capsules. The capsules contained suitable amounts of the active ingredient.

Example 9

Description of Manufacturing

A pharmaceutical formulation according to the present invention, in the form of capsules, having the following composition was prepared:

| | Granulate 0.18% | |
|---|---|---|
| Solid excipients | Compound B calcium[1] | 0.19% |
| | Mannitol | 65.0% |
| | Microcrystalline cellulose | 32.0% |
| Granulation fluid | Calcium acetate | 3.00% |
| | Water (50.0% of solid excipients) | na[2] |

[1]The compound given above may be replaced with another compound of the present invention.
[2]The water is removed during drying.

A preblend of compound B calcium, mannitol and microcrystalline cellulose was prepared. The preblend was wet granulated with am aqueous calcium acetate solution. All excipients required for capsule filling were present in the granulation step. The resulting granulate was dried in a conventional manner and passed through a screen of suitable size. The dry granules were filled into capsules. The capsules contained suitable amounts of the active ingredient

Example 10

Description of Manufacturing

A pharmaceutical formulation according to the present invention, in the form of tablets, having the following composition was prepared:

| | Granulate 0.19% | |
|---|---|---|
| Solid excipients | Mannitol | 30.0% |
| | Pregelatinised starch | 66.8% |
| | Sodium carbonate | 2.84% |
| Granulation fluid | Compound A sodium[1] | 0.20% |
| | Sodium carbonate | 0.20% |
| | Water (35.8% of solid excipients) | na[2] |
| | Tablets | |
| | Compound A sodium Granulate 0.19% | 93.1% |
| | Sodium stearyl fumarate | 0.94% |
| | Coating suspension | |
| | Opadry 03B28796 White | 6.00% |

[1]The compound given above may be replaced with another compound of the present invention.
[2]The water is removed during drying.

Compound A sodium was dissolved in aqueous sodium carbonate and wet granulated together with mannitol, pregelatinised starch and additional sodium carbonate. All excipients required for tabletting except the lubricant were present in the granulation step. The resulting granulate was dried in a conventional manner and passed through a screen of suitable size. The dry granules were mixed well with sodium stearyl fumarate and the mixture obtained was compressed to tablets. The tablets were coated with a film on Opadry 03B 28796 White. The tablets contained suitable amounts of the active ingredient.

Example 11

Description of Manufacturing

A pharmaceutical formulation according to the present invention, in the form of tablets, having the following composition was prepared:

| | Granulate 0.18% | |
|---|---|---|
| Solid excipients | Mannitol | 32.0% |
| | Macrocrystalline cellulose | 65.8% |
| Granulation fluid | Compound A sodium[1] | 0.20% |
| | Sodium carbonate | 0.20% |
| | Sodium hydrogen carbonate | 1.80% |
| | Water (50.0% of solid excipients) | na[2] |
| | Tablets | |
| | Compound A sodium Granulate 0.18% | 99.0% |
| | Sodium stearyl fumarate | 1.00% |

[1]The compound given above may be replaced with another compound of the present invention.
[2]The water is removed during drying.

Compound A sodium was dissolved in aqueous solution of a sodium carbonate/sodium hydrogen carbonate mixture and wet granulated together with mannitol and microclystalline cellulose. All excipients required for tabletting except the lubricant were present in the granulation step. The resulting granulate was dried in a conventional manner and passed through a screen of suitable size. The dry granules were mixed well with sodium stearyl fumarate and the mixture obtained was compressed to tablets. The tablets contained suitable amounts of the active ingredient.

Example 12

Description of Manufacturing

A pharmaceutical formulation according to the present invention, in the form of tablets, having the following composition was prepared:

|  |  | Granulate 0.18% |
|---|---|---|
| Solid excipients | Mannitol | 48.5% |
|  | Calcium sulphate dihydrate | 48.3% |
|  | Sodium carbonate | 3.02% |
| Granulation fluid | Compound A sodium[1] | 0.19% |
|  | Sodium carbonate | 0.01% |
|  | Water (6.7% of solid excipients) | na[2] |
|  | Tablets |  |
|  | Compound A sodium Granulate 0.18% | 99.0% |
|  | Sodium stearyl fumarate | 1.00% |

[1]The compound given above may be replaced with another compound of the present invention.
[2]The water is removed during drying.

Compound A sodium was dissolved in aqueous sodium carbonate solution and wet granulated together with mannitol, calcium sulphate dihydrate and additional sodium carbonate. All excipients required for tabletting except the lubricant were present in the granulation step and the resulting granule was dried in a conventional manner. The dry granules were mixed well with sodium stearyl fumarate and the mixture obtained was compressed to tablets. The tablets contained suitable amounts of the active ingredient.

What is claimed is:

1. A stable solid pharmaceutical composition consisting essentially of an effective amount of a salt of formula (II)

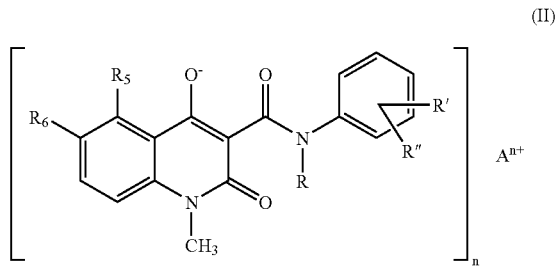

wherein n is an integer of 1, 2 or 3; $A^{n+}$ is a mono- or multivalent metal cation selected from $Li^+$, $Na^+$, $K^+$, $Mg^{2+}$, $Ca^{2+}$, $Mn^{2+}$, $Cu^{2+}$, $Zn^{2+}$, $Al^{3+}$ and $Fe^{3+}$;

R is a straight or branched $C_1$-$C_4$-alkyl or -alkenyl or a cyclic $C_3$-$C_4$-alkyl;

R5 is a straight or branched, saturated or unsaturated $C_1$-$C_4$-alkyl or -alkenyl, a cyclic $C_3$-$C_4$-alkyl, a straight or branched $C_1$-$C_4$-alkylthio, a cyclic $C_3$-$C_4$-alkylthio, a straight or branched $C_1$-$C_4$-alkylsulfinyl, a cyclic $C_3$-$C_4$-alkylsulfinyl, fluoro, chloro, bromo, trifluoromethyl or trifluoromethoxy; and R6 is hydrogen; or R5 and R6 taken together are methylenedioxy;

R' is hydrogen, a straight or branched, saturated or unsaturated $C_1$-$C_4$-alkyl or -alkenyl, a cyclic $C_3$-$C_4$-alkyl, a straight or branched $C_1$-$C_4$-alkoxy, a cyclic $C_3$-$C_4$-alkoxy, fluoro, chloro, bromo or trifluoromethyl; and R" is hydrogen, fluoro or chloro, with the proviso that R" is fluoro or chloro only when R' is fluoro or chloro;

an alkaline-reacting component, or a salt with a divalent metal cation; and at least one pharmaceutical excipient;

wherein said salt of formula (II) is essentially stable during storage at room temperature for a period of at least 3 years.

2. The solid pharmaceutical composition of claim 1 having a pH maintained above 8 by the alkaline-reacting component.

3. The solid pharmaceutical composition of claim 1 wherein n is 1 and $A^{n+}$ is $Li^+$, $Na^+$ or $K^+$.

4. The solid pharmaceutical composition of claim 3 wherein $A^{n+}$ is $Na^+$.

5. The solid pharmaceutical composition of claim 1 wherein the salt of formula (II) is a salt of N-ethyl-N-phenyl- 5-chloro- 1,2-dihydro- 4-hydroxy- 1-methyl- 2-oxo- 3-quinolinecarboxamide.

6. The solid pharmaceutical composition of claim 3 wherein the salt of formula (II) is a salt of N-ethyl-N-phenyl- 5-chloro- 1,2-dihydro- 4-hydroxy- 1-methyl- 2-oxo- 3-quinolinecarboxamide.

7. The solid pharmaceutical composition of claim 4 wherein the salt of formula (II) is a salt of N-ethyl -N-phenyl- 5-chloro- 1,2-dihydro- 4-hydroxy- 1-methyl- 2-oxo- 3-quinolinecarboxamide.

8. The solid pharmaceutical composition of claim 1 wherein the salt of formula (II) is a salt of N-ethyl-N-phenyl- 5-ethyl- 1,2-dihydro- 4-hydroxy- 1-methyl- 2-oxo- 3-quinolinecarboxamide.

9. The solid pharmaceutical composition of claim 3 wherein the salt of formula (II) is a salt of N-ethyl-N-phenyl- 5-ethyl- 1,2-dihydro- 4-hydroxy- 1-methyl- 2-oxo- 3-quinolinecarboxamide.

10. The solid pharmaceutical composition of claim 4 wherein the salt of formula (II) is a salt of N-ethyl-N-phenyl- 5-ethyl- 1,2-dihydro- 4-hydroxy- 1-methyl- 2-oxo- 3-quinolinecarboxamide.

11. The solid pharmaceutical composition of claim 8 wherein n is 2 and $A^{n+}$ is $Ca^{2+}$, or $Zn^{2+}$.

12. The solid pharmaceutical composition of claim 11 wherein $A^{n+}$ is $Ca^{2+}$.

13. The solid pharmaceutical composition of claim 1 wherein the salt of formula (II) is a lithium or calcium salt of N-ethyl-N-phenyl- 5-chloro- 1,2-dihydro- 4-hydroxy- 1-methyl- 2-oxo- 3-quinolinecarboxamide or a lithium, calcium or zinc salt of N-ethyl N-phenyl- 5-ethyl- 1,2-dihydro- 4-hydroxy- 1-methyl- 2-oxo- 3-quinolinecarboxamide.

14. The solid pharmaceutical composition of claim 1 which is in the form of a capsule or a tablet.

15. The solid pharmaceutical composition of claim 1 wherein the salt of formula (II) is present in an amount of 0.01 to 10% by weight of the composition.

16. The solid pharmaceutical composition of claim 1 wherein the salt of formula (II) is present in an amount of 0.1 to 2% by weight of the composition.

17. The solid pharmaceutical composition of claim 1 wherein the alkaline-reacting component is selected from sodium, potassium, calcium and aluminum salts of acetic acid, carbonic acid, citric acid and phosphoric acid.

18. The solid pharmaceutical composition of claim 1 wherein the alkaline-reacting component is present in an amount of 0.1 to 99% by weight of the composition.

19. The solid pharmaceutical composition of claim 1 wherein the alkaline-reacting component is present in an amount of 1 to 20% by weight of the composition.

20. The solid pharmaceutical composition of claim 1 wherein the salt with a divalent metal cation is calcium acetate.

21. The solid pharmaceutical composition of claim 20 wherein the calcium acetate is present in an amount of 1 to 10% by weight of the composition.

22. The solid pharmaceutical composition of claim 1, wherein the pharmaceutical excipient is selected from solid powdered carriers, binders, disintegrants and lubricating agents.

23. The solid pharmaceutical composition of claim 22 wherein the solid powdered carriers are selected from mannitol, microcrystalline cellulose, calcium hydrogen phosphate, calcium sulphate and starch.

24. The solid pharmaceutical composition of claim 22 wherein the binders are selected from polyvinylpyrrolidone, starch and hydroxypropyl methylcellulose.

25. The solid pharmaceutical composition of claim 22 wherein the disintegrants are selected from sodium croscarmellose, sodium starch glycollate and polyvinylpyrrolidone.

26. The solid pharmaceutical composition of claim 22 wherein the lubricating agents are selected from magnesium stearate, sodium stearyl fumarate, talc and hydrogenated vegetable oil.

27. A process for stabilizing a salt of formula (II)

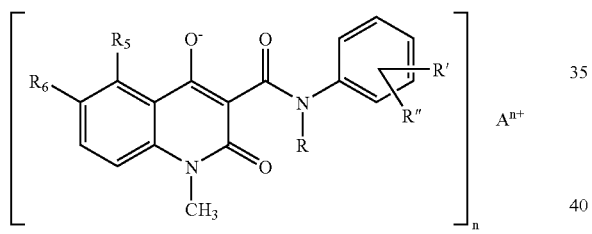

(II)

wherein n is 2; $A^{n+}$ is $Ca^{2+}$;
R is a straight or branched $C_1$-$C_4$-alkyl or -alkenyl or a cyclic $C_3$-$C_4$-alkyl;
R5 is a straight or branched, saturated or unsaturated $C_1$-$C_4$-alkyl or -alkenyl, a cyclic $C_3$-$C_4$-alkyl, a straight or branched $C_1$-$C_4$-alkylthio, a cyclic $C_3$-$C_4$-alkylthio, a straight or branched $C_1$-$C_4$-alkylsulfinyl, a cyclic $C_3$-$C_4$-alkylsulfinyl, fluoro, chloro, bromo, trifluoromethyl or trifluoromethoxy; and
R6 is hydrogen; or
R5 and R6 taken together are methylenedioxy;
R' is hydrogen, a straight or branched, saturated or unsaturated $C_1$-$C_4$-alkyl or -alkenyl, a cyclic $C_3$-$C_4$-alkyl, a straight or branched $C_1$-$C_4$-alkoxy, a cyclic $C_3$-$C_4$-alkoxy, fluoro, chloro, bromo or trifluoromethyl; and
R" is hydrogen, fluoro or chloro, with the proviso that R" is fluoro or chloro only when R' is fluoro or chloro;
by spraying a calcium acetate solution onto a mixture of the calcium salt of formula (II) and at least one pharmaceutical excipient,
said process giving a salt of formula (II) which is essentially stable in a solid pharmaceutical composition during storage at room temperature for a period of at least 3 years.

28. A process for stabilizing a salt of formula (II)

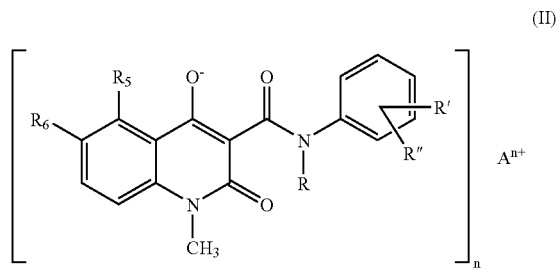

(II)

wherein n is an integer of 2 or 3 ; $A^{2+}$ is a multivalent metal cation selected from $Ca^{2+}$, $Zn^{2+}$ and $Fe^{3+}$;
R is a straight or branched $C_1$-$C_4$-alkyl or -alkenyl or a cyclic $C_3$-$C_4$-alkyl;
R5 is a straight or branched, saturated or unsaturated $C_1$-$C_4$alkyl or -alkenyl, a cyclic $C_3$-$C_4$-alkyl, a straight or branched -$C_1C_4$-alkylthio, a cyclic $C_3$-$C_4$-alkylthio, a straight or branched $C_1$-$C_4$-alkylsulfinyl, a cyclic $C_3$-$C_4$-alkylsulfinyl, fluoro, chloro, bromo, trifluoromethyl or trifluoromethoxy; and
R6 is hydrogen; or
R5 and R6 taken together are methylenedioxy;
R' is hydrogen, a straight or branched, saturated or unsaturated $C_1$-$C_4$-alkyl or alkenyl, a cyclic $C_3$-$C_4$-alkyl, a straight or branched $C_1$-$C_4$-alkoxy, a cyclic $C_3$-$C_4$-alkoxy, fluoro, chloro, bromo or trifluoromethyl; and
R" is hydrogen, fluoro or chloro, with the proviso that R" is fluoro or chloro only when R' is fluoro or chloro;
by spraying a solution of an alkaline-reacting component onto a pharmaceutical excipient or a mixture of pharmaceutical excipients,
granulating to proper consistency,
drying the granulate so obtained and mixing the dried granulate with the salt of formula (II),
said process giving a salt of formula (II) which is essentially stable in a solid pharmaceutical composition during storage at room temperature for a period of at least 3 years.

29. A process for stabilizing a salt of formula (II)

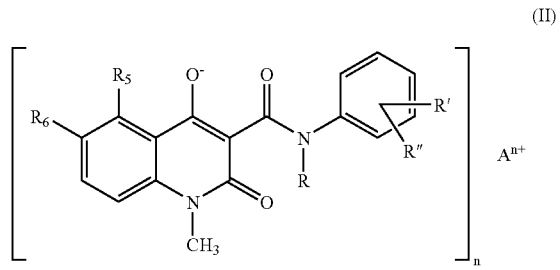

(II)

wherein n is 1; $A^{2+}$ is a monovalent metal cation selected from $Li^+$, $Na^+$ and $K^+$;
R is a straight or branched $C_1$-$C_4$-alkyl or -alkenyl or a cyclic $C_3$-$C_4$alkyl;
R5 is a straight or branched, saturated or unsaturated $C_1$-$C_4$-alkyl or -alkenyl, a cyclic $C_3$-$C_4$-alkyl, a straight or branched $C_1$-$C_4$-alkylthio, a cyclic $C_3$-$C_4$-alkylthio, a straight or branched $C_1C_4$-alkylsulfinyl, a cyclic $C_3C_4$-alkylsulfinyl, fluoro, chloro, bromo, trifluoromethyl or trifluoromethoxy; and R6 is hydrogen; or R5 and R6 taken together are methylenedioxy;

R' is hydrogen, a straight or branched, saturated or unsaturated $C_1$-$C_4$-alkyl or -alkenyl, a cyclic $C_3$-$C_4$-alkyl, a straight or branched $C_1$-$C_4$-alkoxy, a cyclic $C_3$-$C_4$-alkoxy, fluoro, chloro, bromo or trifluoromethyl; and R" is hydrogen, fluoro or chloro, with the proviso that R" is fluoro or chloro only when R' is fluoro or chloro;

by spraying a solution of the compound of formula (II) and an alkaline-reacting component onto a pharmaceutical excipient or a mixture of pharmaceutical excipients, said process giving a salt of formula (II) which is essentially stable in a solid pharmaceutical composition during storage at room temperature for a period of at least 3 years.

30. A stable solid pharmaceutical composition comprising an effective amount of a salt of formula (II)

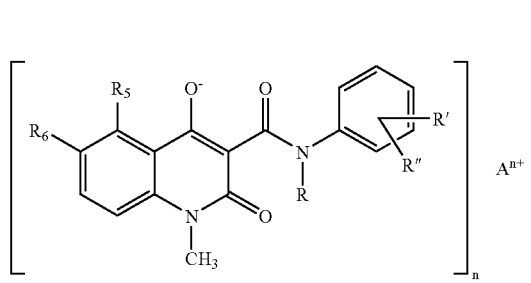

(II)

wherein n is an integer of 1, 2 or 3; $A^{n+}$ is a mono- or multivalent metal cation selected from $Li^+$, $Na^+$, $K^+$, $Mg^{2+}$, $Ca^{2+}$, $Mn^{2+}$, $Cu^{2+}$, $Zn^{2+}$, $Al^{3+}$ and $Fe^{3+}$;

R is a straight or branched $C_1$-$C_4$-alkyl or -alkenyl or a cyclic $C_3$-$C_4$-alkyl;

R5 is a straight or branched, saturated or unsaturated $C_1$-$C_4$-alkyl or -alkenyl, a cyclic $C_3$-$C_4$-alkyl, a straight or branched $C_1$-$C_4$-alkylthio, a cyclic $C_3$-$C_4$-alkylthio, a straight or branched $C_1$-$C_4$-alkylsulfinyl, a cyclic $C_3$-$C_4$-alkylsulfinyl, fluoro, chloro, bromo, trifluoromethyl or trifluoromethoxy; and R6 is hydrogen; or R5 and R6 taken together are methylenedioxy;

R' is hydrogen, a straight or branched, saturated or unsaturated $C_1$-$C_4$-alkyl or -alkenyl, a cyclic $C_3$-$C_4$-alkyl, a straight or branched $C_1$-$C_4$-alkoxy, a cyclic $C_3$-$C_4$-alkoxy, fluoro. chloro, bromo or trifluoromethyl; and R" is hydrogen, fluoro or chloro, with the proviso that R" is fluoro or chloro only when R' is fluoro or chloro;

at least one pharmaceutical excipient; and a component which neutralizes protons diffusing from the pharmaceutical excipients.

31. The stable solid pharmaceutical composition of claim 30 wherein the component which neutralizes protons diffusing from the pharmaceutical excipients is an alkaline-reacting component.

32. The stable solid pharmaceutical composition of claim 31 wherein the alkaline reacting component is sodium carbonate.

* * * * *

UNITED STATES PATENT AND TRADEMARK OFFICE
CERTIFICATE OF CORRECTION

PATENT NO. : 7,589,208 B2  Page 1 of 1
APPLICATION NO. : 11/050441
DATED : September 15, 2009
INVENTOR(S) : Jansson et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1023 days.

Signed and Sealed this

Twenty-first Day of September, 2010

David J. Kappos
*Director of the United States Patent and Trademark Office*